US00PP15954P3

(12) United States Plant Patent
Schräder

(10) Patent No.: US PP15,954 P3
(45) Date of Patent: Sep. 13, 2005

(54) **VARIETY OF *SANVITALIA* PLANT NAMED 'SUMSAN 01'**

(50) Latin Name: ***Sanvitalia* hybrid**
Varietal Denomination: Sumsan 01

(75) Inventor: Ralf Schräder, Lüdinghausen (DE)

(73) Assignee: Grunewald Veredlings, B.V. (NL)

( * ) Notice: Subject to any disclaimer, the term of this patent is extended or adjusted under 35 U.S.C. 154(b) by 108 days.

(21) Appl. No.: 10/378,476

(22) Filed: Mar. 3, 2003

(65) Prior Publication Data

US 2004/0177421 P1 Sep. 9, 2004

(51) Int. Cl.[7] ..... A01H 5/00

(52) U.S. Cl. ..... Plt./263

(58) Field of Search ..... Plt./263

(56) References Cited

PUBLICATIONS

UPOV–Rom hit on 'Sumsan 01', Plant Variety Database, 2004/02.*

* cited by examiner

*Primary Examiner*—Anne Marie Grunberg
(74) *Attorney, Agent, or Firm*—Webb Ziesenheim Logsdon Orkin & Hanson, P.C.

(57) ABSTRACT

A new and distinct early flowering *Sanvitalia* plant with bright yellow-orange colored flowers.

2 Drawing Sheets

Botanical classification: *Sanvitalia* hybrid.
Varietal denomination: 'Sumsan 01'.

BACKGROUND OF THE INVENTION

The present invention comprises a new and distinct cultivar of *Sanvitalia* plant known by the varietal name 'Sumsan 01'. The new variety was discovered in June 2000 in a selected breeding program in Lüdinghausen, Germany. The new variety was selected from a cross of proprietary unpatented breeding plants Seedling 64 (female parent) and Seedling 11 (male parent). The new variety has a leaf size similar to its parents, but differs in flower markings from both parents. The new variety has a similar flower color and vigor to *Sanvitalia* variety 'Lucky Penny' (unpatented), but has more leaf pubescence. The new variety was first asexually reproduced in September 2001 by cuttings in L üdinghausen, Germany. The new variety has been trial and field tested at Lüdinghausen and has been found to retain its distinctive characteristics and remain true to type through successive propagations.

The following traits distinguish 'Sumsan 01' as a new and distinct cultivar:

1. The size of the capitulum.
2. The color of the ray floret.
3. Leaf pubescence.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
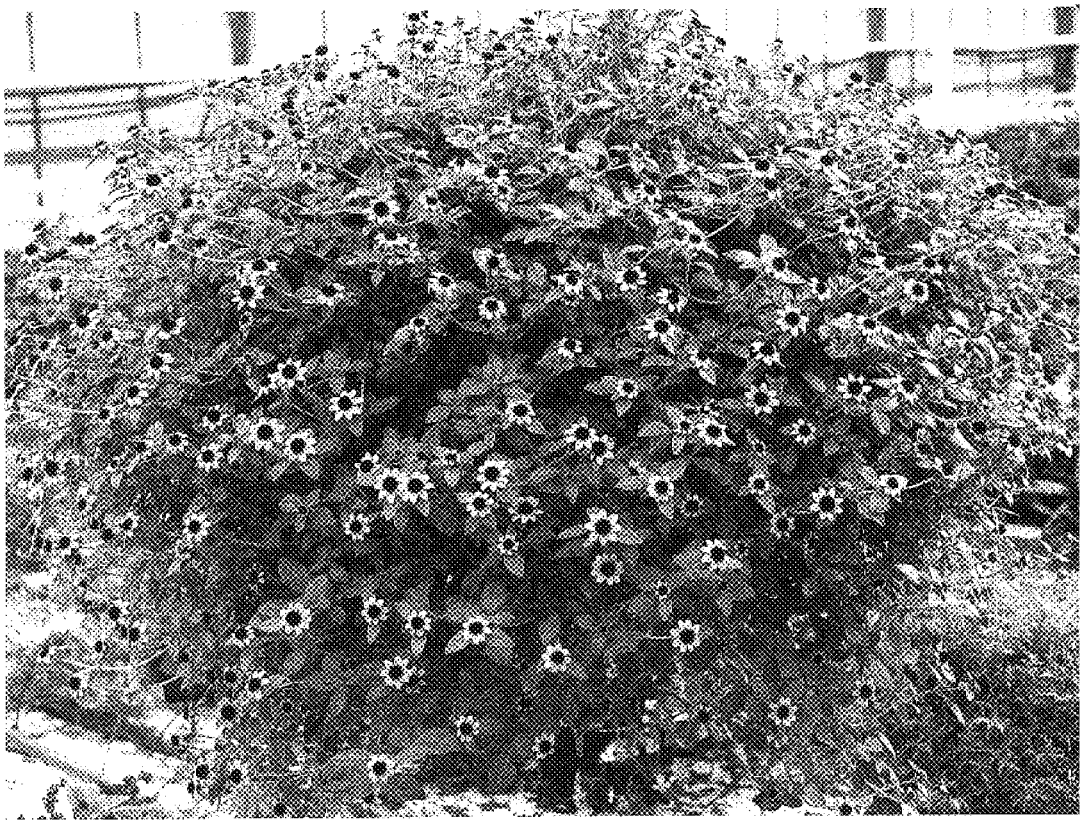
FIG. 1 is a photograph of the plant.
Figure 2:
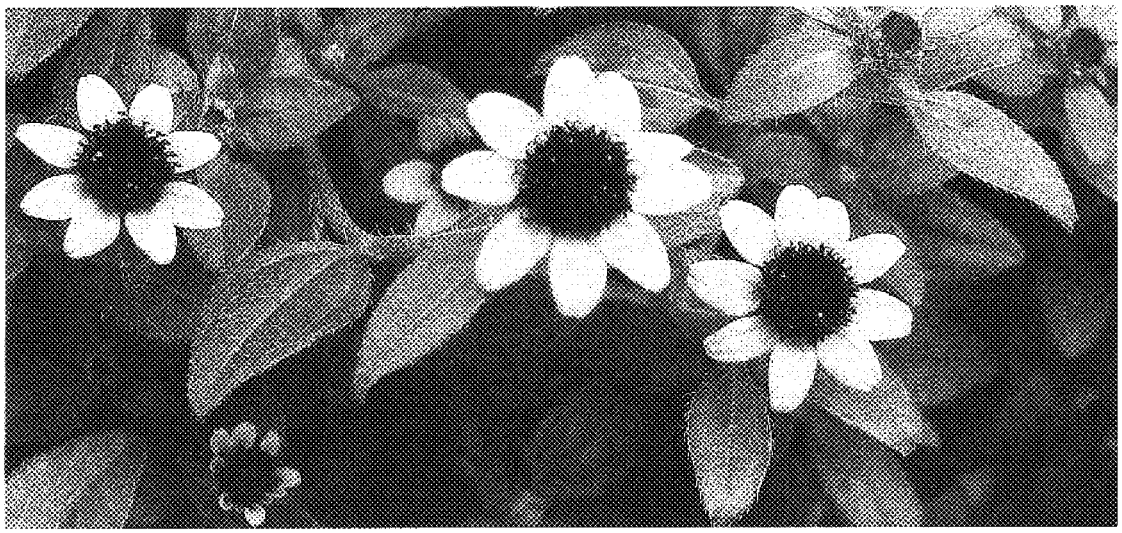
FIG. 2 is a close up view of the blooms of the new plant.

The following detailed description sets forth characteristics of the new cultivar. The data which defines these characteristics were collected by asexual reproductions by cuttings carried out in Lüdinghausen, Germany. Plants for the description were 16 weeks old. The color readings were taken in a greenhouse under natural light. Color references are primarily to the 1996 R.H.S. Colour Chart of The Royal Horticultural Society of London.

PLANT

Form: Spreading.
Height (from soil to top of flowers): 40–50 cm at the end of summer.
Diameter: 50 cm after 4–5 months.
Vigor: Strong; similar to the *Sanvitalia* variety 'Aztekengold' (unpatented).
Roots:
- *Habit.*—Upright.
- *Time to initiate roots.*—14 days at 20° C.
- *Time to develop roots.*—35 days at 20° C.

Time to produce finished flowering plant: About 14 weeks in a 10.5 cm container.
Branching habit: Hanging.
Lateral branches:
- *Color.*—145A.
- *Texture.*—Solid.
- *Diameter.*—1 mm.
- *Internode length.*—Approximately 3.5 cm.

Foliage:
- *Size of leaf.*—Length: Approximately 2 cm. Width: Approximately 0.9 cm.
- *Shape of leaf.*—Lanceolate.
- *Shape of apex.*—Obtuse.
- *Shape of base.*—Obtuse.
- *Texture.*—Light pubescence.
- *Aspect.*—Weak.

*Margin.*—Entire.
*Color.*—Young leaves: Upper surface: 137C. Lower surface: 137D. Mature leaves: Upper surface: 137A. Lower surface: 146B.
*Petiole.*—Length: 3 mm. Diameter: 0.8 mm. Color: 145B.
*Veins.*—Venation type: Parallel. Color: Upper surface: 145A. Lower surface: 145A.

FLOWER

Natural flowering season: Spring to autumn.
Bud (characteristics at day one of opening):
*Shape.*—Semi-globose cup with upperside open.
*Diameter.*—2 mm.
*Length.*—2 mm.
*Color.*—144B.
Corolla:
*Form.*—Actinomorphic.
*Petals/lobes.*—Number: 8. Length: 5–7 mm. Width: 3–5 mm. Shape: Obtuse. Aspect: Weak with 3 waves. Margin: Entire with one incision on the top. Texture and appearance: Weak.
*Color.*—When opening: Upper surface: 15A. Lower surface: 15D. Fully opened: Upper surface: Dark ring inside 15A with 13B outside. Lower surface: 15D with green veins.
*Throat.*—Color: 200B. Texture: Canescent.
*Tube color.*—142B.
Calyx:
*Form.*—Cupped.
*Length.*—3 mm.
*Diameter.*—0.5 mm.
*Sepal shape.*—Lanceolate.
*Sepal margin.*—Entire.
*Sepal texture.*—Puberulous.
*Sepal color.*—Upper surface: 137C. Lower surface: 137D.
Disease resistance: No resistance to diseases noted to date.
Fragrance: None.
Temperature tolerance: From 0° C. to 35° C.
Lasting quality: Continuous.

REPRODUCTIVE ORGANS

Stamens:
*Number.*—Numerous; approximately 200.
*Filament length.*—2 mm.
*Pollen.*—Color: Yellow. Amount: Plentiful.
Pistil:
*Length.*—2 mm.
*Style.*—Length: 1.5 mm. Color: 187A.
*Stigma.*—Shape: Figure eight. Color: 187A.
Fruit: None observed.
Seeds:
*Production.*—Minimal.
*Length.*—Approximately 4.0 mm.
*Width.*—Approximately 2.0 mm.
*Shape.*—Lanceolate.
*Color.*—Inside: Depends on freshness. When fresh, the color is white. When stored for serveral months, the color is 201A. Margin: 159A.

I claim:

1. A new and distinct variety of *Sanvitalia* plant substantially as shown and described.

* * * * *